US005505709A

United States Patent [19]
Funderburk et al.

[11] Patent Number: 5,505,709
[45] Date of Patent: Apr. 9, 1996

[54] MATED INFUSION PUMP AND SYRINGE

[75] Inventors: Jeffery V. Funderburk, Granada Hills; Matthew Jordan, Los Angeles; Deborah C. McIntyre, Agoura Hills, all of Calif.

[73] Assignee: MiniMed, Inc., a Delaware Corporation, Sylmar, Calif.

[21] Appl. No.: 306,418

[22] Filed: Sep. 15, 1994

[51] Int. Cl.[6] ............................................. A61M 5/145
[52] U.S. Cl. ..................................... 604/155; 604/151
[58] Field of Search ............................. 604/152, 154, 604/156, 151; 128/DIG. 1, DIG. 12, DIG. 13

[56] References Cited

U.S. PATENT DOCUMENTS

| | | | |
|---|---|---|---|
| 4,416,662 | 11/1983 | Dore et al. | 604/154 |
| 4,424,720 | 1/1984 | Bucchianeri | 128/DIG. 1 |
| 4,435,173 | 3/1984 | Siposs et al. | 604/155 |
| 4,562,751 | 1/1986 | Nason et al. | |
| 4,613,327 | 9/1986 | Tegrarian et al. | 128/DIG. 12 |
| 4,678,408 | 7/1987 | Nason et al. | |
| 4,685,903 | 8/1987 | Cable et al. | |
| 4,804,368 | 2/1989 | Skakoon et al. | 128/DIG. 1 |
| 4,978,335 | 12/1990 | Arthur, III | 604/155 |
| 5,006,112 | 4/1991 | Metzner | 604/155 |
| 5,080,653 | 1/1992 | Voss et al. | |
| 5,097,122 | 3/1992 | Colman et al. | |
| 5,101,679 | 4/1992 | Smith et al. | 604/155 |
| 5,139,484 | 8/1992 | Hazon et al. | 604/155 |
| 5,269,762 | 12/1993 | Armbruster et al. | 604/155 |
| 5,290,239 | 3/1994 | Classey et al. | 604/131 |

*Primary Examiner*—Paul J. Hirsch
*Attorney, Agent, or Firm*—Kelly Bauersfeld & Lowry

[57] ABSTRACT

An improved medication infusion pump is provided of the type for receiving and supporting a medication-containing syringe, wherein the pump and syringe include matingly interfitted components to ensure use of the pump with a compatible and correctly installed syringe. The infusion pump comprises a pump housing defining a syringe compartment for receiving and supporting the syringe, in combination with a drive member for engaging and programmably displacing a syringe plunger to administer medication to a patient. In one preferred form, the drive member and plunger include a matingly interfitting tab and notch which are engaged when the syringe is fully and properly positioned within the syringe compartment. In another form, the tab and notch are formed on the syringe plunger and a portion of the pump housing.

8 Claims, 2 Drawing Sheets

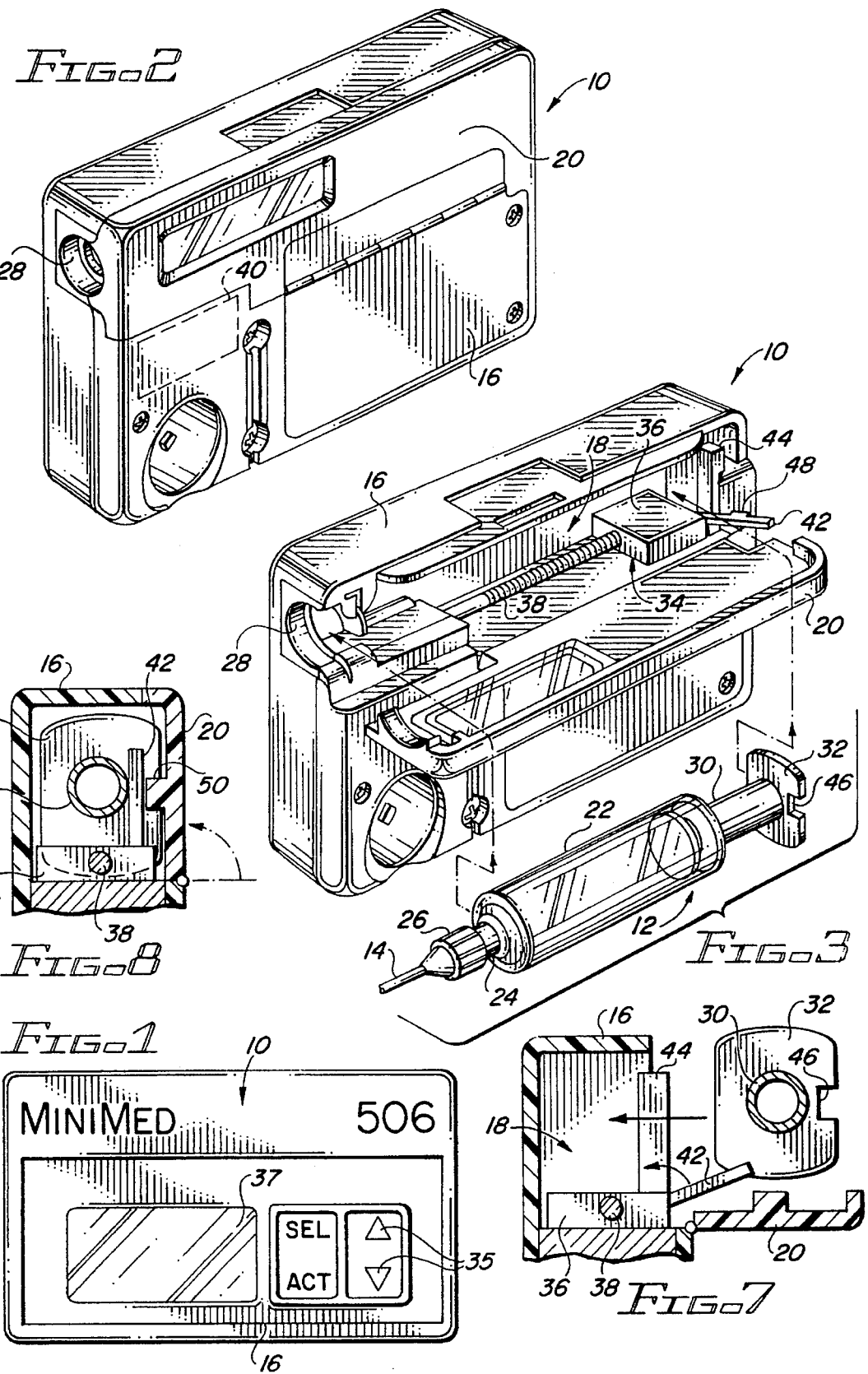

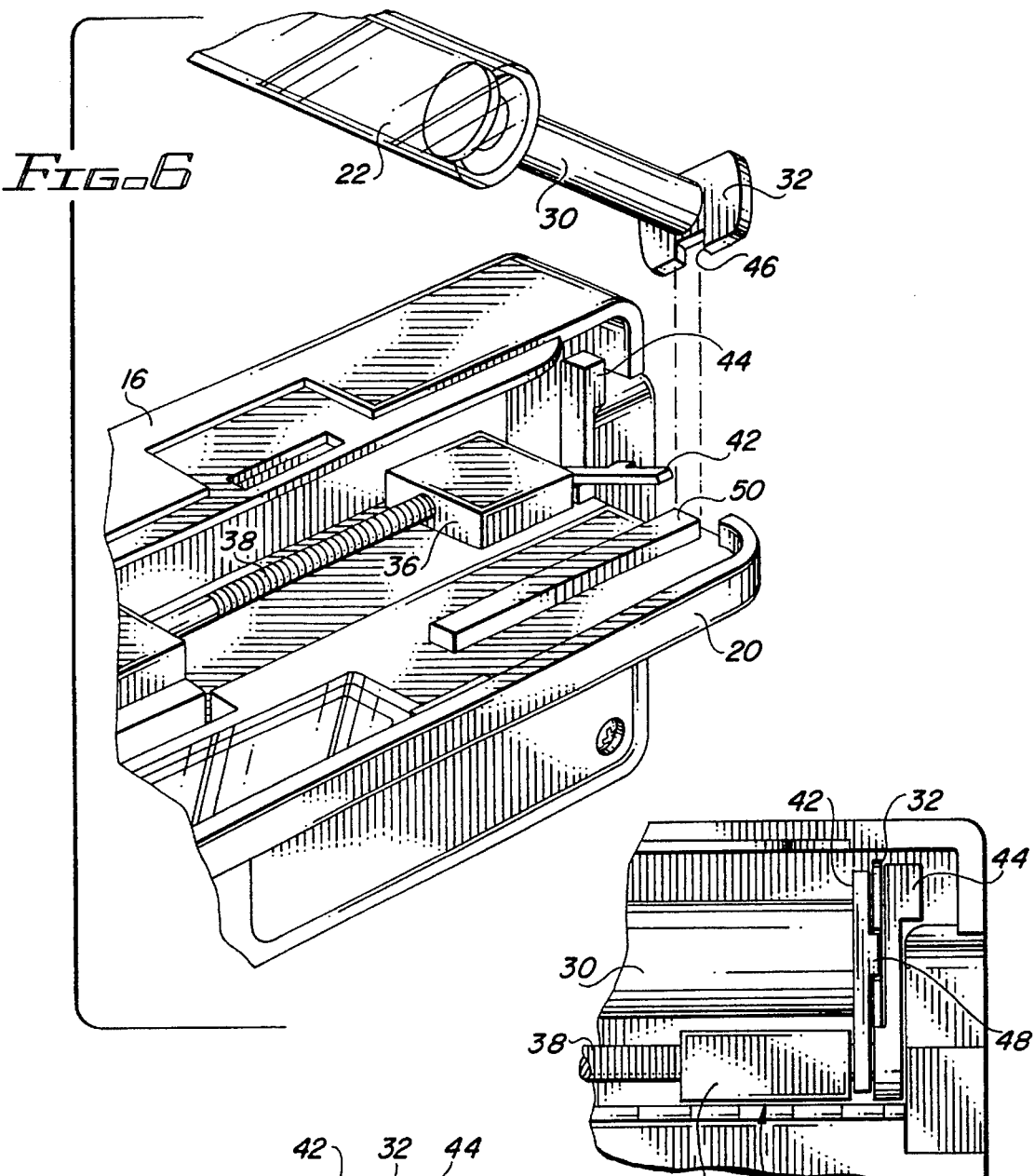
FIG. 6
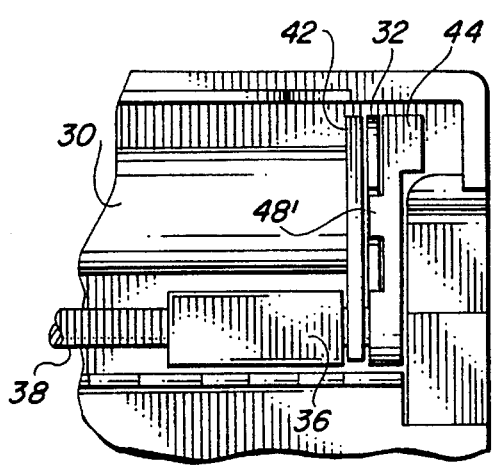
FIG. 4
FIG. 5

MATED INFUSION PUMP AND SYRINGE

BACKGROUND OF THE INVENTION

This invention relates generally to improvements in infusion pumps of the type used for controlled delivery of medication to a patient. More specifically, this invention relates to an improved infusion pump and related medication-containing syringe, wherein the pump and syringe include matingly interfitting components to ensure pump use with a compatible and correctly installed syringe.

Infusion pump devices and systems are relatively well known in the medical arts, for use in delivering or dispensing a prescribed medication such as insulin to a patient. In one form, such devices comprise a relatively compact housing adapted to receive and support a syringe carrying a prescribed medication for administration to the patient through infusion tubing and an associated catheter or the like. The infusion pump includes a small drive motor connected via a lead screw assembly for motor-driven advancement of a syringe piston plunger to administer the medication to the patient. Programmable control means are normally provided for operating the drive motor continuously or at periodic intervals to obtain a closely controlled and accurate delivery of medication over an extended period of time. Such infusion pumps are utilized to administer insulin and other medications, with exemplary pump constructions being shown and described in U.S. Pat. Nos. 4,562,751; 4,678,408; 4,685,903; 4,562,751; 4,678,408; 4,685,903; 5,080,653; and 5,097,122, which are incorporated herein by reference.

Infusion pumps of the general type described above have provided significant advantages and benefits with respect to accurate delivery of medication over an extended time period. The infusion pump is often designed to be extremely compact and thus may be adapted to be carried by the patient, for example, by means of a belt clip or the like. As a result, important medication can be administered with precision and in an automated manner, without significant restriction on the patient's mobility or life-style.

To achieve accurate and reliable delivery of medication to the patient in response to motor-driven advancement of the syringe piston plunger, it can be extremely important to use a syringe which is designed to meet a narrow set of operational specifications which are compatible with the syringe pump. That is, variations in the size and shape of the syringe, friction forces attributable to sliding plunger seals, etc., can result in significant variations in the amount of medication administered in response to operation of the pump drive motor. In addition, incorrect installation of the syringe into the pump housing can result in undesirable inaccuracte delivery or nondelivery of the medication.

The present invention overcomes these problems and disadvantages by providing matingly interfitting components on the pump and the syringe to prevent pump usage with an incompatible syringe and further to ensure that the syringe is fully and correctly installed prior to use.

SUMMARY OF THE INVENTION

In accordance with the invention, a medication infusion pump is provided for use with a medication-containing syringe to obtained precision controlled delivery of the medication through infusion tubing or the like to a patient. The pump and syringe include matingly interfitting components to ensure pump usage with a compatible and correctly installed syringe.

The infusion pump comprises a compact pump housing having an elongated syringe compartment formed therein for receiving and supporting a medication-containing syringe barrel and associated piston plunger. A pump drive motor is operated in a programmable manner to dispense medication from the syringe. The drive motor includes a mechanical output such as a lead screw assembly linked to the piston plunger for controlled plunger advancement into the syringe barrel. The lead screw assembly includes one or more drive arms for engaging the syringe plunger, as by engaging a flange located at a rear end of the plunger.

In one preferred form of the invention, the mating components on the pump and syringe include a tab formed on one of the drive arms of the lead screw assembly, and a notch formed in one edge of the plunger flange. Drive engagement between the lead screw assembly and the plunger flange requires seated reception of the tab within the notch, whereby an incompatible syringe omitting the notch on the plunger flange cannot be used. Moreover, a compatible syringe also cannot be used, unless the syringe is fully and properly seated within the syringe compartment whereat the tab can be matingly fitted into the notch. A hinged door is normally provided for closing the syringe compartment, and cannot be closed unless mating interengagement between the tab and notch is achieved.

In one alternative preferred form of the invention, the interfitting tab and notch can be formed on other structures. For example, the tab can be formed as an elongated rib on a portion of the pump housing within the syringe compartment, for mating engagement with the notch on the plunger flange.

Other features and advantages of the present invention will become more apparent from the following detailed description, taken in conjunction with the accompanying drawings which illustrate, by way of example, the principles of the invention.

BRIEF DESCRIPTION OF THE DRAWINGS

The accompanying drawings illustrate the invention. In such drawings:

FIG. 1 is a front elevation view illustrating a medication infusion pump adapted for controlled delivery of medication to a patient;

FIG. 2 is an enlarged rear perspective view of the infusion pump of FIG. 1;

FIG. 3 is an exploded rear perspective view of the infusion pump of FIG. 2, illustrating a syringe compartment for receiving and supporting a medication-containing syringe, and wherein the pump and syringe include matingly interfitting components in accordance with the invention;

FIG. 4 is an enlarged fragmented elevational view depicting mated interfitted engagement between the pump and syringe;

FIG. 5 is an enlarged fragmented elevational view similar to FIG. 4, and illustrating an alternative preferred form of the invention;

FIG. 6 is an enlarged fragmented perspective view similar to a portion of FIG. 3, and illustrating a further alternative preferred form of the invention;

FIG. 7 is an enlarged fragmented vertical sectional view illustrating installation of the medication-containing syringe into the infusion pump syringe compartment of FIG. 6; and FIG. 8 is a fragmented sectional view similar to FIG. 7, and illustrating the syringe fully installed into the syringe compartment within the infusion pump.

DETAILED DESCRIPTION OF THE PREFERRED EMBODIMENTS

As shown in the exemplary drawings, a medication infusion pump referred to generally by the reference numeral 10 is provided for controlled administration of medication to a patient. The infusion pump 10 is adapted to receive and support a medication-containing syringe 12 (FIG. 3), and includes means for automatically and programmably operating the syringe to deliver the medication through infusion tubing 14 or the like to the patient. In accordance with the invention, the infusion pump 10 and the syringe 12 include matingly interfitting components to insure that the syringe and pump are compatibly designed and further to ensure that the syringe is fully and properly installed within the pump.

The infusion pump 10 has an overall construction and operation which is generally known in the art. More specifically, with reference to FIGS. 1–3, the infusion pump 10 comprises a relatively compact pump housing 16 defining an elongated syringe compartment 18 (FIG. 3) adapted to receive and support the syringe 12 charged with a selected medication, such as insulin, to be administered to a patient. FIG. 3 shows a hinged access door 20 in an open position to permit slide-fit or drop-in placement of the syringe 12 into the syringe compartment 18, after which the door 20 can be pivoted to a closed position (FIG. 2) during normal operation of the infusion pump. In general terms, the medication-containing syringe 12 includes a syringe barrel 22 joined at a nose end thereof to a luer neck 24 having a size and shape for connection to a luer fitting 26. As shown best in FIG. 3, the luer neck 24 is adapted for seated reception within an outlet port 28 formed in the pump housing 16, and the luer fitting 26 is coupled via the infusion tubing 14 and catheter (not shown) for transcutaneous infusion of medication to the patient.

A syringe piston plunger 30 extends from the aft end of the syringe barrel 22, and may be advanced into the barrel to deliver the medication therefrom. In this regard, the illustrative plunger 30 terminates at a distal end in a radially enlarged flange 32 adapted for engagement with a lead screw assembly 34 for programmably controlled motorized displacement of the piston plunger 30 to administer medication through the infusion tubing 14. FIG. 3 shows the lead screw assembly 34 to include a lead screw nut 36 carried on a lead screw 38 which is adapted to be driven by an appropriate drive motor 40 (FIG. 1). The plunger flange 32 has a size and shape for slide fit reception into a slotted region formed on the lead screw nut 36, with the flange 32 positioned axially between a front retainer arm 42 and a rear drive arm 44. The front retainer arms 42, 44 are pivotally mounted on the lead screw nut 36 to permit outward swinging thereof as shown in FIG. 3 to a position enabling syringe installation into the syringe compartment. Thereafter, the arms 42, 44 are pivoted to an operative position disposed on opposite sides of the plunger flange 32.

During normal pump operation, advancement of the lead screw nut 36 in response to motor-driven rotation of the lead screw causes the rear drive arm 44 to bear against the piston plunger flange 32, thereby administering medication from the syringe 12. The front retainer arm 42 is provided to prevent plunger creep or overtravel as might occur, for example, in response to pressure forces within the syringe barrel 22. The lead screw 38 is operated in a programmed manner wherein the program can be set and revised by means of input keys 35 and a display 37 located at the front of the housing 16 (FIG. 1).

In accordance with the present invention, the plunger flange 32 is shaped to include a laterally open notch 46 at a predetermined position, and having a predetermined size and shape. This notch 46 is adapted for mating reception of a tab 48. As shown in FIGS. 3 and 4, the tab 48 may be formed on the front retainer arm 42 of the lead screw assembly 34. When the syringe 12, including the flanged notch 46, is fully and properly seated within the syringe compartment 18, the front retainer arm 42 can be pivoted to the operational position by virtue of the tab 48 being matingly received into the notch 46. Conversely, if a syringe lacking the notch 46 is used, or if the syringe is otherwise improperly positioned within the compartment 18, the retainer arm 42 cannot be moved to the operational position. Subsequent closure of the access door 20 is thus prevented and thereby provides clear indication to the user that an improper syringe has been installed, or otherwise that a compatible syringe has been improperly installed.

FIG. 5 illustrates one alternative form of the invention, wherein a tab 48' is formed on the rear drive arm 44, rather than on the front retainer arm 42, as viewed in FIGS. 3 and 4. The tab 48' on the drive arm 38 functions in the same manner as described above to ensure that a compatible syringe is used and is properly installed prior to attempted operation of the infusion pump.

FIGS. 6–8 show a further alternative preferred form of the invention, wherein an elongated rib or key 50 is formed on a portion of the pump housing 16 defining one wall of the syringe compartment 18, and the tab 48 as shown in FIGS. 3–4, (or the tab 48' as viewed in FIG. 5) on the lead screw assembly is omitted. In this embodiment, the rib or key 50 is positioned for mating or seated reception into the flange notch 46 when the syringe is fully and properly installed, and the access door 20 is closed. Attempted use of an incompatible syringe lacking the flange notch 46 or an otherwise improperly installed syringe, will result in an inability to close the access door 20.

The present invention thus provides a safeguard against use of a medication-containing syringe which may be of a nonstandard size and/or incompatible configuration, and thus should not be used with the medication infusion pump. The matingly interfitted components on the pump housing and syringe ensure use of a syringe having a compatible design, and further that the syringe will be properly and fully installed prior to use.

A variety of further modifications and improvements to the present invention will be apparent to those skilled in the art. For example, it will be understood that the interfitting tab and notch structures may be positioned at any convenient location on the pump and syringe to achieve the objectives of the present invention. Accordingly, no limitation on the invention is intended by way of the foregoing description and accompanying drawings, except as set forth in the appended claims.

What is claimed is:

1. In an infusion pump system including an infusion pump having a pump housing defining a syringe compartment for receiving and supporting a syringe, and an access door movable between open and closed positions, said syringe having a syringe barrel and a plunger received therein, said pump including drive means for controllably moving said plunger relative to said barrel to deliver medication from said syringe, the improvement comprising:

tab and notch means formed on said pump and syringe for mated interfitting engagement with each other when said syringe is received into the syringe compartment, said tab and notch means when engaged permitting closure of said access door when said syringe is received within the syringe compartment, said tab and notch means when disengaged preventing closure of said access door when said syringe is received within the syringe compartment.

2. The combination of claim 1 wherein said tab and notch means comprises a tab formed on said pump and a notch formed in said syringe.

3. An infusion pump system, comprising:

a syringe having a syringe barrel adapted to be filled with a selected medication and a plunger slidably received into said barrel and movable therein to deliver the medication therefrom; and an infusion pump including a pump housing defining a syringe compartment for receiving and supporting said syringe, an access door movable between open and closed positions, and drive means for engaging and controllably moving said plunger to deliver the medication;

said pump and said syringe including tab and notch means for mated interfitted engagement with each other when said syringe is received into the syringe compartment, said tab and notch means when engaged permitting closure of said access door when said syringe is received within the syringe compartment, said tab and notch means when disengaged preventing closure of said access door when said syringe is received within the syringe compartment.

4. The system of claim 3 wherein said tab and notch means comprises a tab formed on said pump and a notch formed in said syringe.

5. The system of claim 4 wherein said plunger includes an enlarged flange disposed generally at an outboard end thereof, said notch being formed in said flange.

6. The system of claim 5 wherein said tab is formed on said drive means.

7. The system of claim 5 wherein said drive means comprises a lead screw assembly having at least one drive arm pivotally movable between a first position permitting said syringe to be placed into the syringe compartment and a second position in engagement with said plunger, said tab being formed on said drive arm and received into said notch when said drive arm is in the second position.

8. The system of claim 5 wherein said tab comprises an elongated rib formed along a portion of said housing defining the syringe compartment.

\* \* \* \* \*